(12) United States Patent
Furukawa (10) Patent No.: US 8,104,513 B2
(45) Date of Patent: Jan. 31, 2012

(54) GAS FLOW PATH SWITCHING UNITS

(75) Inventor: Masanao Furukawa, Kyoto (JP)

(73) Assignee: Shimadzu Corporation, Kyoto-Shi (JP)

( * ) Notice: Subject to any disclaimer, the term of this patent is extended or adjusted under 35 U.S.C. 154(b) by 937 days.

(21) Appl. No.: 12/117,424

(22) Filed: May 8, 2008

(65) Prior Publication Data

US 2009/0101017 A1 Apr. 23, 2009

(30) Foreign Application Priority Data

Oct. 19, 2007 (JP) .................................. 2007-271978

(51) Int. Cl.
*F15B 21/00* (2006.01)
(52) U.S. Cl. ..................... 137/806; 137/825; 137/883
(58) Field of Classification Search ............ 137/487.5, 137/599.01, 806, 833, 825, 829, 883, 861, 137/862, 869; 96/101–106
See application file for complete search history.

(56) References Cited

U.S. PATENT DOCUMENTS

| | | | | |
|---|---|---|---|---|
| 3,238,961 | A * | 3/1966 | Hatch, Jr. ................... | 137/816 |
| 3,374,799 | A * | 3/1968 | Lyman ........................ | 137/13 |
| 3,712,028 | A * | 1/1973 | Deans ......................... | 95/82 |
| 6,447,581 | B2 * | 9/2002 | Gellert et al. ............... | 96/102 |
| 6,497,252 | B1 * | 12/2002 | Kohler et al. ............... | 137/828 |
| 7,137,286 | B2 * | 11/2006 | Furukawa .................... | 73/23.42 |
| 2002/0033193 | A1 * | 3/2002 | McNeely et al. ............ | 137/825 |
| 2007/0089603 | A1 * | 4/2007 | Emmons et al. ............. | 95/82 |
| 2007/0163962 | A1 | 7/2007 | Bidlingmeyer et al. | |

FOREIGN PATENT DOCUMENTS

| | | |
|---|---|---|
| JP | 11-248694 A | 9/1999 |
| JP | 2000-179714 A | 6/2000 |
| JP | 2006-064646 A | 3/2006 |
| JP | 2006-329703 | * 12/2006 |
| JP | 2007-187663 A | 7/2007 |

OTHER PUBLICATIONS

Machine translation of JP 2006-329703.*

* cited by examiner

*Primary Examiner* — Craig Schneider
*Assistant Examiner* — Jessica Cahill
(74) *Attorney, Agent, or Firm* — Sughrue Mion, PLLC

(57) ABSTRACT

Disclosed is a gas flow path switching unit including a gas passage section with a target gas passage for allowing said target gas to pass therethrough. The target gas passage includes a main passage having a proximal end serving as said gas inlet and a number n of branch passages each provided with a respective gas outlet at a terminal end thereof. The branch passages are formed by repeating two or more times a branching process of branching said main passage into two sub passages at a branch point at a distal end of said main passage and further branching at least one of said sub passages into two sub-sub passages at a branch point defined by a distal end of said sub passage. The target gas passage also includes at least a number n of switching-gas supply passages connected to respective intermediate positions of said n branch passages.

9 Claims, 6 Drawing Sheets

FIG. 8B
PRIOR ART

GAS FLOW PATH SWITCHING UNITS

BACKGROUND OF THE INVENTION

1. Field of the Invention

The present invention relates to a gas flow path switching unit suitable for a multidimensional gas chromatograph.

2. Description of the Related Art

In a multidimensional gas chromatograph that uses a combination of a plurality of columns with different separation characteristics and a plurality of detectors arranged side by side, a gas flow path switching unit is essential in order to allow a sample gas introduced via a certain passage to be selectively sent to a desired one of two or more branch passages. If the gas flow path switching unit is designed such that a movable portion of a three-way valve or the like resides inside a gas passage, it will face problems, such as increase in dead volume, and absorption of components of a sample gas by a material (e.g., grease) for providing enhanced movability to the movable portion, or, on the contrary, incorporation of such an undesirable material into the sample gas. From this point of view, a specific structure, called "Deans type", has been used as the gas flow path switching unit (see, for example, JP 11-248694A, JP 2000-179714A and JP 2007-187663A).

Figure 8A:
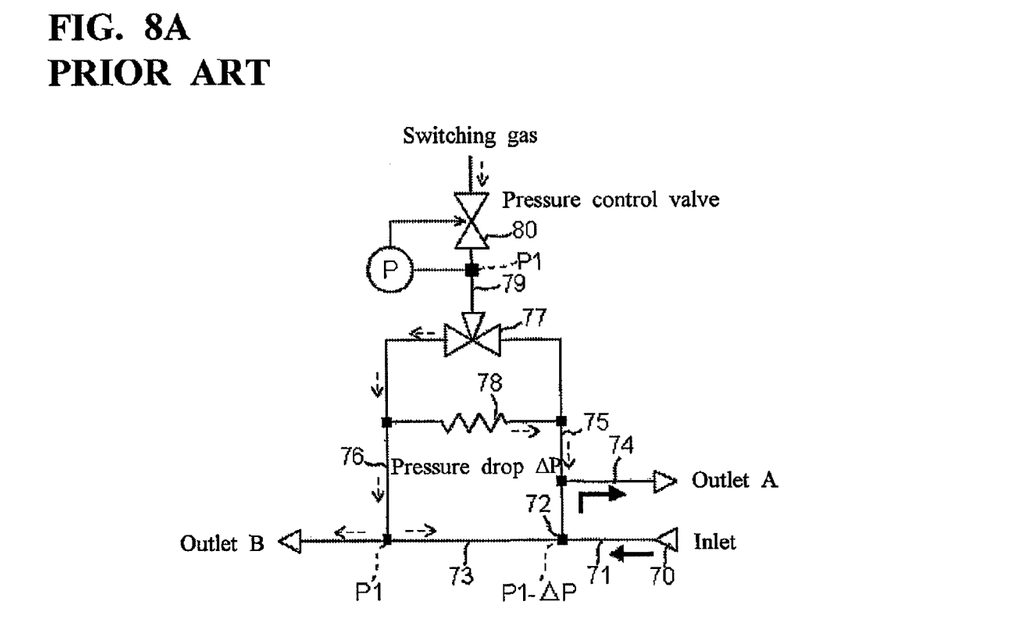
FIGS. 8A and 8B are schematic diagrams showing a basic structure of a conventional Deans-type gas flow path switching unit.
Figure 8B:
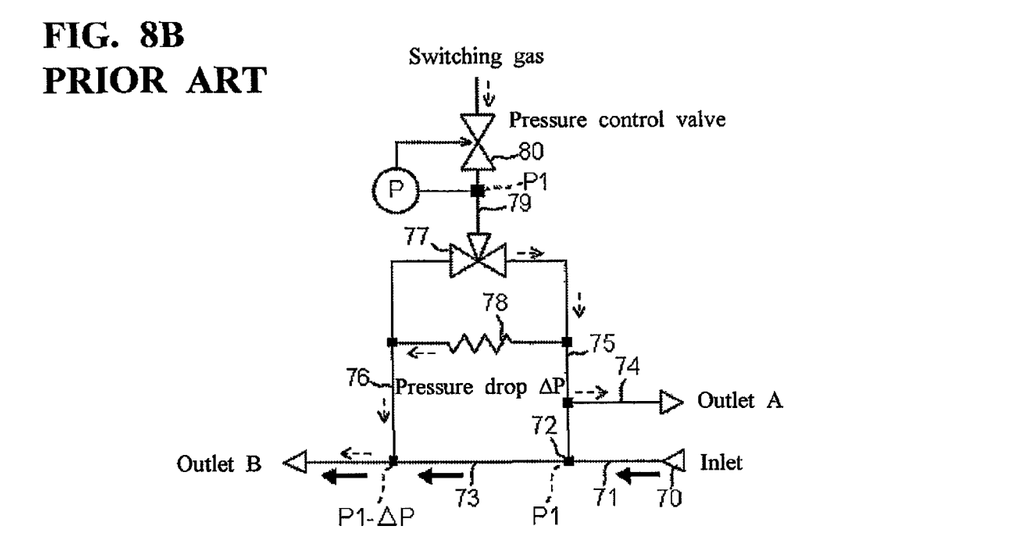

FIGS. 8A and 8B are schematic diagrams showing a basic structure of a Deans-type gas flow path switching unit. In this unit, a main passage 71 having one end serving as an gas inlet 70 for allowing a sample gas to be supplied therethrough is branched into a first branch passage 74 directed toward a gas outlet A, and a second branch passage 73 directed toward a gas outlet B, at a branch point 72. A first switching-gas supply passage 75 is connected between an intermediate position of the first branch passage 74 and one of two exits of a three-way switching valve 77, and a second switching-gas supply passage 76 is connected between an intermediate position of the second branch passage 73 and the other exit of the three-way switching valve 77. Further, a resistance tube having a given flow resistance is connected between the first and second switching-gas supply passages 75, 76. A switching-gas source passage 79 having a pressure control valve 80 interposed therein is connected to an entrance of the three-way switching valve 77.

The three-way switching valve 77 is composed of a solenoid valve, and is operable to selectively connect either one of the first and second switching-gas supply passages 75, 76 to the switching-gas source passage 79. The pressure control valve 80 is provided with a pressure sensor for detecting a gas pressure on a downstream side of the pressure control valve 80, and designed such that a valve opening degree thereof is automatically adjusted to allow the gas pressure to be maintained at a predetermined value.

An operation of the Deans-type gas flow path switching unit will be described below. Under control of the pressure control valve 80, the gas pressure on the downstream side thereof is now maintained at P1. In a state when the switching-gas source passage 79 is connected to the second switching-gas supply passage 76 by the three-way switching value 77, a switching gas flows as indicated by the arrowed dotted-lines in FIG. 8A. Given that a flow resistance in each passage is zero, and a pressure drop during passing through the resistance tube 78 is ΔP, a gas pressure on the side of the gas outlet B becomes P1, and a gas pressure on the side of the gas outlet A becomes P1−ΔP. A sample gas supplied from the gas inlet 70 to the main passage 71 flows from the branch point 72 into one of the branch passages 73, 74 which has a lower pressure. Thus, the sample gas is discharged from the outlet A via the first branch passage 74, as indicated by the arrowed thick-lines in FIG. 8A.

Then, when the three-way switching value 77 is switched to connect the switching-gas source passage 79 to the first switching-gas supply passage 75, the switching gas flows as indicated by the arrowed dotted-lines in FIG. 8B, so that the gas pressure on the side the outlet A becomes P1, and the gas pressure on the side of the outlet B becomes P1−ΔP. Therefore, as indicated by the arrowed thick-lines in FIG. 8B, the sample gas supplied from the gas inlet 70 to the main passage 71 is discharged from the outlet B via the second branch passage 73.

As above, the Deans-type gas flow path switching unit is designed to change a flow direction of the switching gas by the three-way switching value 77, so as to allow an outlet of the sample gas introduced from the gas inlet 70 to be switched between the gas outlets A, B.

Lately, as gas chromatographic analysis techniques have progressed, there has been a demand for a system capable of introducing an elution component from an analytical column, into any of three or more different detectors, such as a mass spectrometer, a hydrogen flame ionization detector (FID), a flame photometric detector (FPD), and an electron capture detector (ECD), in an appropriately switchable manner. In order to meet this demand, a gas flow path switching unit must be capable of allowing a sample gas to switch between any of three or more flow paths. However, if it is attempted to achieve the switching between the three or more flow paths using the conventional Deans-type gas flow path switching unit, the number of components and unit cost are undesirably increased, and other problems, such as failure, gas leakage and absorption of components of a sample gas, are liable to occur.

SUMMARY OF THE INVENTION

In view of the above problems, it is a primary object of the present invention to provide a gas flow path switching unit capable of switching between three or more flow paths, in a simple structure.

In order to achieve the above object, the present invention provides a gas flow path switching unit for setting a gas flow path to allow a target gas introduced from a gas inlet to be discharged from one of a number n of gas outlets, wherein n is an integer equal to or greater than 3, according to control of supply of a switching gas. The gas flow path switching unit comprises a) a target gas passage for allowing the target gas to pass therethrough, which includes a main passage having a proximal end serving as the gas inlet, and a number n of branch passages each provided with a respective one of the gas outlets at a terminal end thereof, wherein the branch passages are formed by repeating two or more times a branching process of branching the main passage into two sub passages at a branch point defined by a distal end of the main passage, and further branching at least one of the sub passages into two sub-sub passages at a branch point defined by a distal end of the sub passage, and b) at least a number n of switching-gas supply passages connected to respective intermediate positions of the n branch passages to supply the switching gas thereto.

In the gas flow path switching unit of the present invention, the target gas can be discharged from a desired one of the n gas outlets, for example, by supplying the switching gas to each of the n switching-gas supply passages connected to the respective intermediate positions of the n branch passages, to control a flow path of the target gas introduced from the gas inlet, according to a flow direction of the switching gas after being supplied into each of the branch passages.

For this purpose, in one embodiment of the present invention, wherein the number of the at least n switching-gas supply passages connected to respective intermediate positions of the n branch passages is n, the gas flow path switching unit may further comprise switching-gas supply control means operable to supply the switching gas to each of the n switching-gas supply passages in such a manner that a gas supply pressure in a specific one of a number n of switching-gas supply ports of the n switching-gas supply passages becomes less than that in the remaining switching-gas supply ports, whereby the target gas is discharged from the gas outlet at the terminal end of one of the branch passages which is supplied with the switching gas from the specific switching-gas supply port at the gas supply pressure less than that in the remaining switching-gas supply ports.

The switching-gas supply control means may include at least a number n−1 of valves each operable to allow the switching gas supplied from a switching-gas entrance thereof to be selectively discharged from one of two switching-gas exits thereof, and at least a number n−1 of resistance tubes each connecting between the two switching-gas exits of a corresponding one of the valves.

Each of the resistance tubes is designed to cause a pressure drop in the switching gas during passing therethrough. According to a flow path-switching operation in each of the valves, a direction of the switching gas passing through the resistance tube associated with the valve is changed (reversed), and thereby a magnitude relationship between respective pressures at opposite ends of the resistance tube is reversed.

Thus, in the gas flow path switching unit according to the above embodiment, the switching-gas supply control means may be operable to switch between two flow paths in each of the at least n−1 valves, in such a manner that, in a plurality of switching-gas flow paths set as a result of the switching, the switching gas reaching the specific switching-gas supply port after passing through a largest number of consecutive ones of the resistance tubes has a gas supply pressure less than that in the remaining switching-gas supply ports.

Each of the valves may be composed of a solenoid valves, and a control circuit for controlling a switching operation in each of the solenoid valves may be provided to allow the target gas introduced from the gas inlet to be selectively supplied to any one of the gas outlets according to electrical control.

Preferably, the gas flow path switching unit of the present invention includes a laminated assembly prepared by sandwiching a first plate-shaped member formed with a cutout portion corresponding to at least a part of the target gas passage and the switching-gas supply passages, between at least two second plate-shaped members. The laminated assembly may be made of a metal material having corrosion resistance, such as stainless steel. This structure makes it possible to achieve a less number of components and a lower cost, as compared with a conventional passage structure where a plurality of pipes are connected to each other using a plurality of T-shaped joints or the like, and advantageously facilitate reduction in size and weight.

This laminated assembly has high flexibility for passage layout and configuration. Thus, in particular, two of the branch passages branched from the common branch point defined by their proximal ends may be arranged at an angle of less than 45 degrees to each other. Generally, an angle between two branch passages is 90 degree. In this case, gas is likely to stagnate when it passes through the branch point while curvingly flowing, and thereby various components contained in the gas are liable to attach onto an inner wall surface of the passages. In contrast, when the angle between the two branch passages is set at less than 45 degrees, gas smoothly passes through the branch point to reduce the risk that the various components attach onto the inner wall surface of the passages. Thus, a multidimensional gas chromatograph using the gas flow path switching unit of the present invention can reduce the risk that components contained in the target gas attach onto the inner wall surface of the passages, so as to achieve enhanced analytical accuracy.

When each of the first and second plate-shaped members is made of metal, a passage-defining inner surface thereof may be subjected to an inactivation treatment, to further reduce the risk of the attachment of the components contained in the gas.

As above, the gas flow path switching unit of the present invention can achieve a flow path-switching operation of allowing a target gas to selectively flow in a desired one of three or more directions, in a simple structure and by a simple control as compared with conventional techniques. In addition, an analysis apparatus using the gas flow path switching unit of the present invention can achieve enhanced analytical accuracy and reproducibility based on the ability to suppress attachment of components contained in the target gas.

DESCRIPTION OF THE EXEMPLARY EMBODIMENTS

Figure 1:
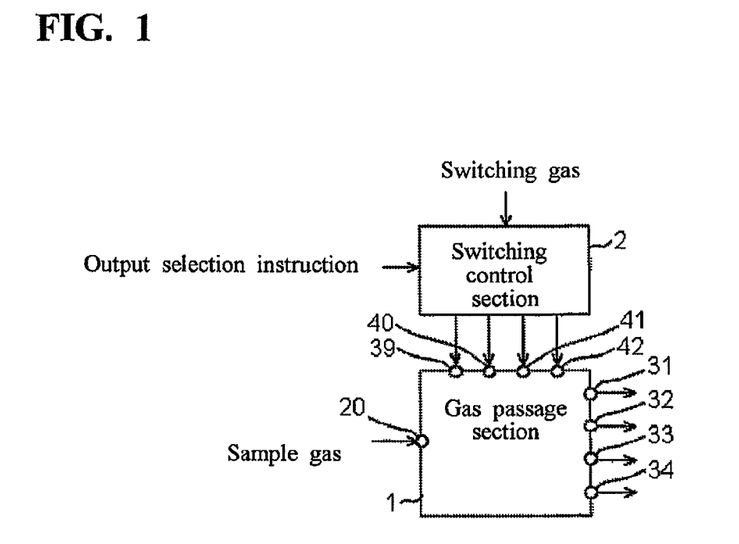
FIG. 1 is a schematic block diagram showing a gas flow path switching unit according to one embodiment of the present invention.
Figure 2:
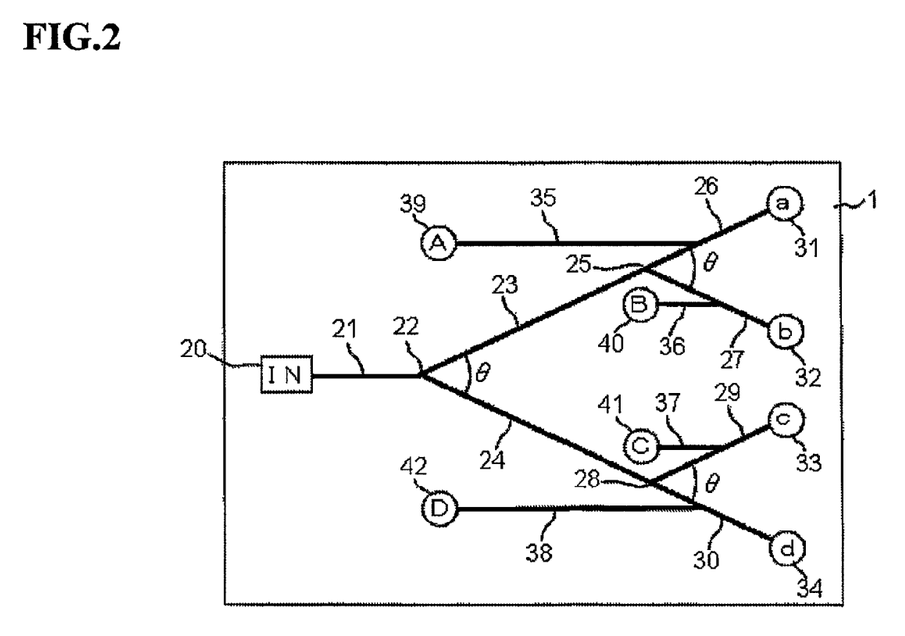
FIG. 2 is a top plan view showing a passage configuration in a gas passage section of the gas flow path switching unit according to one embodiment.
Figure 3:
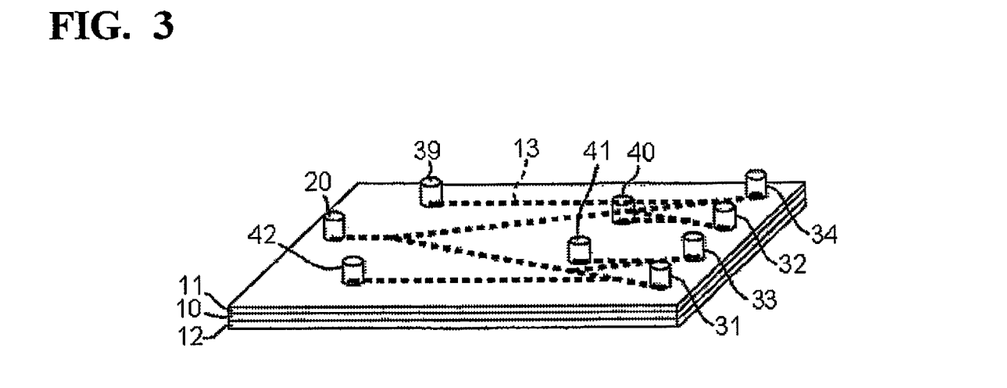
FIG. 3 is a perspective external view showing the gas passage section of the gas flow path switching unit according to one embodiment.
Figure 4:
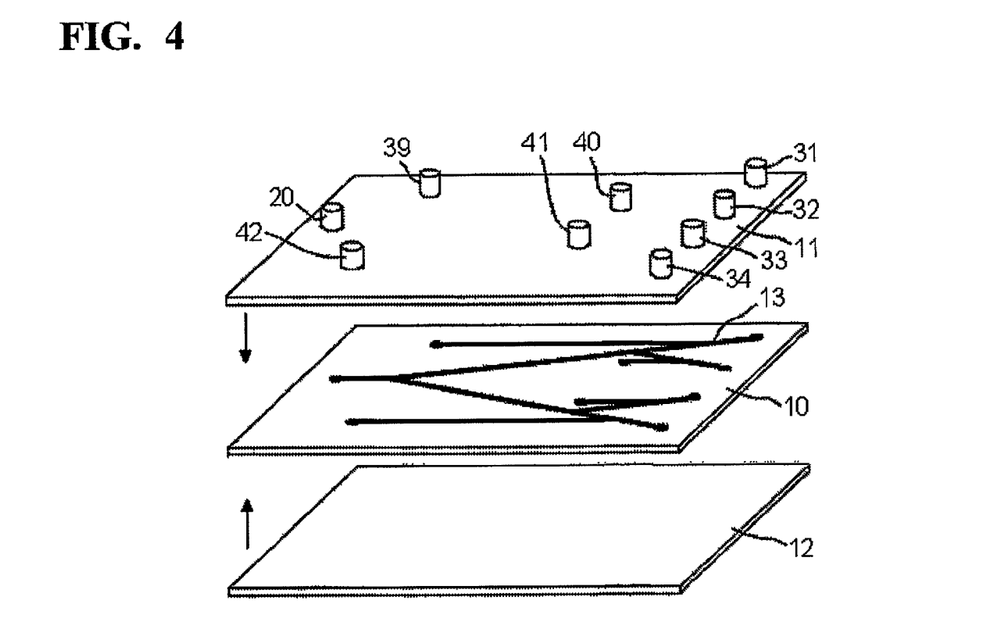
FIG. 4 is an exploded perspective view showing the gas passage section of the gas flow path switching unit according to one embodiment.

With reference to FIGS. 1 to 6B, a gas flow path switching unit according to one embodiment of the present invention will be described. FIG. 1 is a schematic block diagram showing the gas flow path switching unit according to the embodiment, and FIG. 2 is a top plan view showing a passage configuration in a gas passage section of the gas flow path switching unit. FIG. 3 is a perspective external view showing the gas passage section, and FIG. 4 is an exploded perspective view showing the gas passage section. FIGS. 5A to 6B are schematic diagrams for explaining a flow path-switching operation in the gas flow path switching unit according to the embodiment.

The gas flow path switching unit according to this embodiment is designed to have four gas outlets. As shown in FIG. 1, the gas flow path switching unit comprises a gas passage section 1, and a switching control section 2 (serving as switching-gas supply control means). The gas passage section 1 has one gas inlet 20 for introducing a sample gas therethrough, four gas outlets 31, 32, 33, 34, and four switching-gas inlets 39, 40, 41, 42. The switching control section 2 is operable, in response to an output selection instruction signal, to supply a switching gas to the four switching-gas inlets 39, 40, 41, 42 in a distributed manner.

As shown in FIGS. 3 and 4, the gas passage section 1 is composed of a laminated assembly prepared by laminating three metal plates. Specifically, the gas passage section 1 comprises a first plate member 10 formed with a slit 13 vertically penetrating therethrough to serve as an after-mentioned passage, a second plate member 11 formed with eight ports serving as the gas outlets 31, 32, 33, 34 and the switching-gas inlets 39, 40, 41, 42 and disposed on the side of an upper surface of the first plate member 10, and a third plate member 12 composed of a simple flat plate and disposed on the side of a lower surface of the first plate member 10. These three plate members 10, 11, 12 are joined together in a superimposed manner, so that a passage having a height in a thicknesswise direction of the slit 13 of the first plate member 10 is defined between the second and third plate members 11, 12.

As shown in FIG. 2, the gas passage section 1 has a passage configuration which comprises: a main passage 21 having a proximal end serving as the gas inlet 20 ("IN" in FIG. 2); two (i.e., first and second) branch passages 23, 24 extending from a branch point 22 defined by a distal end of the main passage 21; two (i.e., first and second) terminal branch passages 26, 27 extending from a branch point 25 defined by a distal end of the first branch passage 23; and two (i.e., third and fourth) terminal branch passages 29, 30 extending from a branch point 28 defined by a distal end of the second branch passage 24. The four gas outlets 31, 32, 33, 34 ("a" to "d" in FIG. 2) are provided at respective distal ends of the first, second, third and fourth terminal branch passages 26, 27, 29, 30. The two branch (or terminal branch) passages on a downstream side of each of the branch points 22, 25, 28 are arranged at an angle θ of less than 45 degrees with respect to each other. The passage configuration further includes four switching-gas supply passages 35, 36, 37, 38 each having a proximal end serving as a corresponding one of the four switching-gas inlets 39, 40, 41, 42, and a distal end connected to an intermediate position of a corresponding one of the four terminal branch passages 26, 27, 29, 30.

Figure 5A:
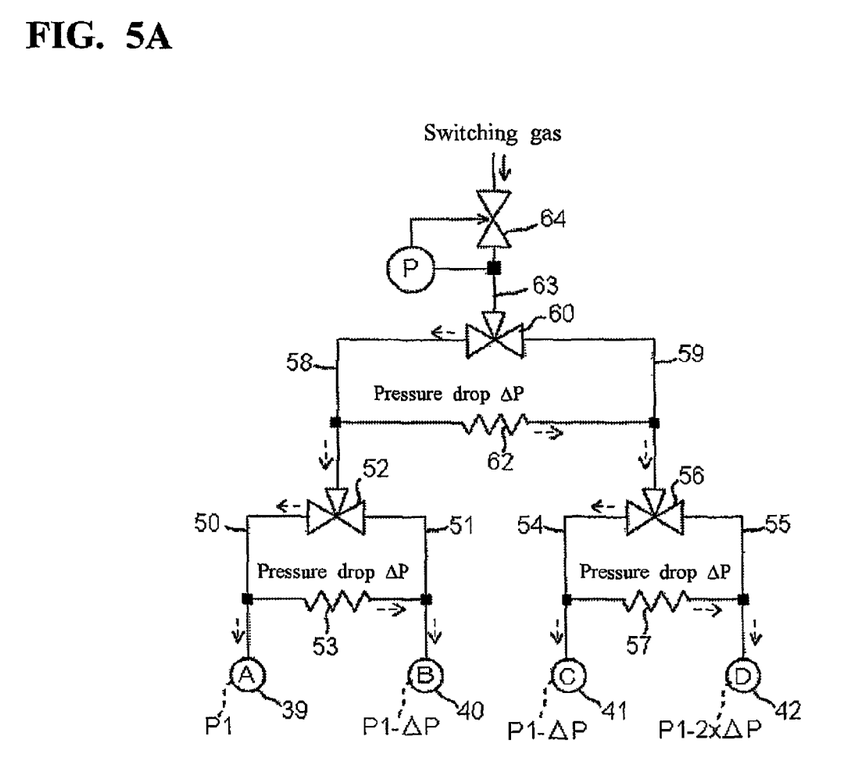
FIGS. 5A and 5B are schematic diagrams for explaining a flow path-switching operation in the gas flow path switching unit according to one embodiment.
Figure 6A:
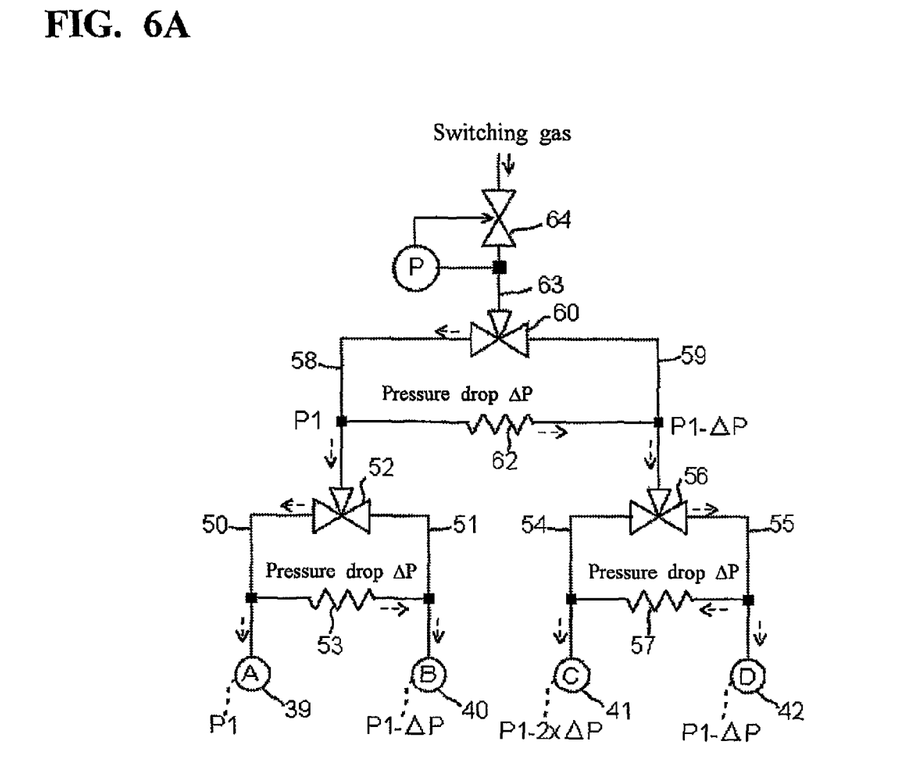
FIGS. 6A and 6B are schematic diagrams for explaining another flow path-switching operation in the gas flow path switching unit according to one embodiment.

As shown in FIGS. 5A and 6A, the switching control section 2 comprises a pressure control valve 64, three (i.e., first, second and third) three-way switching valves 60, 52, 56, and three (i.e., first, second and third) resistance tubes 62, 53, 57 each having the same flow resistance. The pressure control valve 64 is interposed in a switching-gas source passage 63 having a distal end connected to an entrance of the first three-way switching valve 60. The first three-way switching valve 60 has two exits connected to respective proximal ends of two switching-gas distribution passages 58, 59, and the first resistance tube 62 is connected between the two switching-gas distribution passages 58, 59. The switching-gas distribution passage 58 has a distal end connected to an entrance of the second three-way switching valve 52. The second three-way switching valve 52 has two exits connected to respective proximal ends of two switching-gas distribution passages 50, 51, and the second resistance tube 53 is connected between the two switching-gas distribution passages 50, 51. Each of the switching-gas distribution passage 50, 51 has a distal end connected to a corresponding one of the switching-gas inlets 39, 40. The switching-gas distribution passage 59 has a distal end connected to an entrance of the third three-way switching valve 56. The third three-way switching valve 56 has two exits connected to respective proximal ends of two switching-gas distribution passages 54, 55, and the third resistance tube 57 is connected between the two switching-gas distribution passages 54, 55. Each of the switching-gas distribution passage 54, 55 has a distal end connected to a corresponding one of the switching-gas inlets 41, 42.

Although not illustrated, the switching control section 2 includes a control circuit operable to giving a switching control signal for changing a flow direction of the switching gas, to each of the three-way switching valves 60, 52, 58. According to the switching control signal, a flow path-switching operation is performed to allow a sample gas (or any other gas) supplied from the gas inlet 20 to be selectively discharged from a desired one of the four gas outlets 31, 32, 33, 34.

The flow path-switching operation in the gas flow path switching unit according to this embodiment will be specifically described below. When a flow path is set to allow the sample gas to be discharged from a specific one of the gas outlet (a) 31, the gas outlet (b) 32, the gas outlet (c) 33 and the gas outlet (d) 34 in the gas passage section 1, respective connection states of the first to third three-way switching valves 60, 52, 56 are set as shown in the following Table 1.

TABLE 1

| First three-way switching valve | Second three-way switching valve | Third three-way switching valve | Gas outlet |
| --- | --- | --- | --- |
| L | — | L | d |
| L | — | R | c |
| R | L | — | b |
| R | R | — | a |

In Table 1, the "L" means a state when the right exit of the valve is closed, and the left exit of the valve is opened, in FIGS. 5A and 6A (i.e., a state when the sample gas can be discharged from the left exit), and the "R" means a reverse state when the left exit is closed, and the right exit o is opened. The "—" means that the state "R" and "L" of the valve has no impact on a selection of the gas outlet for discharging the sample gas therefrom.

As one example, the control and operation of allowing the sample gas introduced from the gas inlet 20 to be selectively discharged from the gas outlet (d) 34 will be described with reference to FIGS. 5A and 5B.

In this case, the first three-way switching valve 60 is controlled to connect the switching-gas source passage 63 to the switching-gas distribution passage 58, so that the switching gas having a gas pressure P1 adjusted by the pressure control valve 64 is discharged from the exit of the first three-way switching valve 60 into the switching-gas distribution passage 58, as indicated by the arrowed dotted-line in FIG. 5A. This switching gas flows into the entrance of the second three-way switching valve 52, and further flows into the entrance of the third three-way switching valve 56 via the first resistance tube 64 with a pressure drop ΔP caused when it passes through the first resistance tube 64. Thus, the switching gas at the entrance of the second three-way switching valve 52 has a pressure of P1, and the switching gas at the entrance of the third three-way switching valve 56 has a different pressure of P1−ΔP.

The third three-way switching valve 56 is controlled to connect the switching-gas distribution passage 59 to the switching-gas distribution passage 54, so that the switching gas flows into the switching-gas distribution passage 54, as indicated by the arrowed dotted-line in FIG. 5A. This switching gas flows into the switching-gas inlet 41, and further flows into the switching-gas inlet 42 via the third resistance tube 57 with an additional pressure drop $\Delta P$ caused when it passes through the third resistance tube 57. Thus, the switching gas at the switching-gas inlet 41 has a pressure of $P1-\Delta P$, and the switching gas at the switching-gas inlet 42 has a lower pressure of $P1-(2\times\Delta P)$.

In FIG. 5A, the second three-way switching valve 52 is controlled to connect the switching-gas distribution passage 58 to the switching-gas distribution passage 50. Thus, the switching gas at the switching-gas inlet 39 has a pressure of P1, and the switching gas at the switching-gas inlet 40 has a pressure of $P1-\Delta P$. Alternatively, the second three-way switching valve 52 may be reversely controlled to connect the switching-gas distribution passage 58 to the switching-gas distribution passage 51. In this case, the switching gas at the switching-gas inlet 39 has a pressure of $P1-\Delta P$, and the switching gas at the switching-gas inlet 40 has a pressure of P1.

Figure 5B:
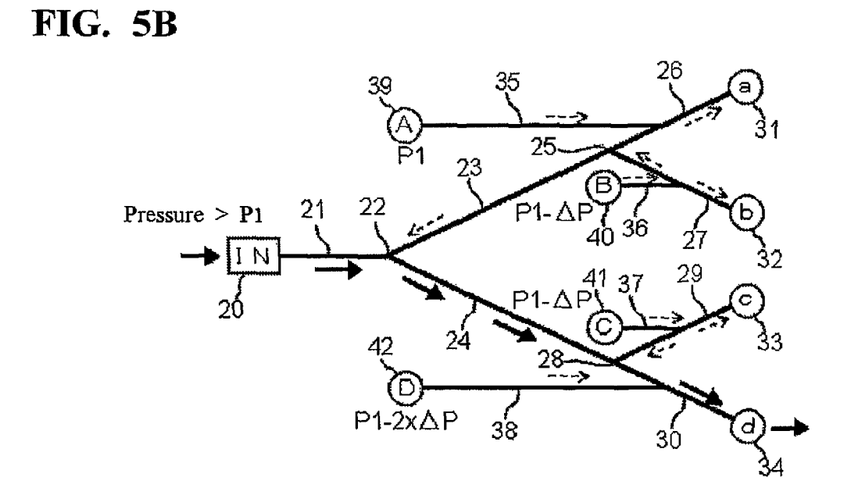

As shown in FIG. 5B, the sample gas is supplied to the gas inlet 20 at a pressure fairly greater than P1. In this state, a pressure of the sample gas at each of the gas outlets 31, 32, 33, 34 is set at zero (Considering that a resistance tube and/or a negative-pressure detector can be connected to the gas outlet, the pressure at the gas outlet may be variously set at an adequate value. What is important is to set the pressure at a value less than $P1-(2\times\Delta P)$). According to the control of the switching control section 2, the switching gas is supplied to the four switching-gas inlets 39, 40, 41, 42 at the respective gas pressures P1, $P1-\Delta P$, $P1-\Delta P$, $P1-(2\times\Delta P)$. Each of the switching gases introduced at the different supply pressures flows through each of the terminal branch passages 26, 27, 29, 30, as indicated by the arrowed dotted-lines in FIG. 5B. The sample gas passing through the main passage 21 flows toward the terminal branch passage 30 connected with the switching-gas supply passage 38 which supplies the switching gas at the lowest pressure. Thus, the sample gas is supplied from the branch passage 24 to the terminal branch passage 30, and discharged from the gas outlet 34. In this case, only the switching gas is discharged from each of the remaining gas outlets 31, 32, 33.

Figure 6B:
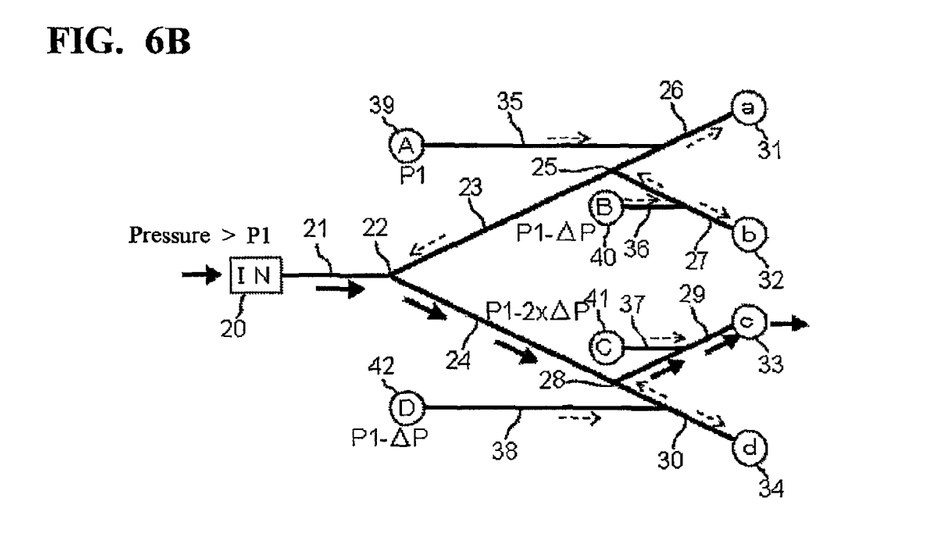

As another example, the control and operation of allowing the sample gas introduced from the gas inlet 20 to be selectively discharged from the gas outlet (c) 33 will be described with reference to FIGS. 6A and 6B.

In this case, while the first three-way switching valve 60 is controlled in the same manner as that in FIG. 5A, the third three-way switching valve 56 is controlled to connect the switching-gas distribution passage 59 to the switching-gas distribution passage 55, in a reverse manner as that in FIG. 5A. In this connection state, a flow direction of the switching gas passing through the third resistance tube 57 is reversed, and thereby respective pressures of the switching gases supplied to the switching-gas inlets 41, 42 are changed to $P1-(2\times\Delta P)$ and $P1-\Delta P$. As a result, each of the switching gases introduced at the different supply pressures flows through each of the terminal branch passages 26, 27, 29, 30, as indicated by the arrowed dotted-lines in FIG. 6B. The sample gas passing through the main passage 21 flows toward the terminal branch passage 29 connected with the switching-gas supply passage 37 which supplies the switching gas at the lowest pressure. Thus, the sample gas is supplied from the branch passage 24 to the terminal branch passage 29, and discharged from the gas outlet 33. In this case, only the switching gas is discharged from each of the remaining gas outlets 31, 32, 34.

The operation of allowing the sample gas to be selectively discharged from the gas outlet 31 or the gas outlet 32 can be performed in a similar manner to that described above. In this way, the sample gas can be extracted from any one of the four gas outlets 31, 32, 33, 34 by changing the respective connection states of the three three-way switching valves 60, 52, 56 as shown in Table 1.

Figure 7:
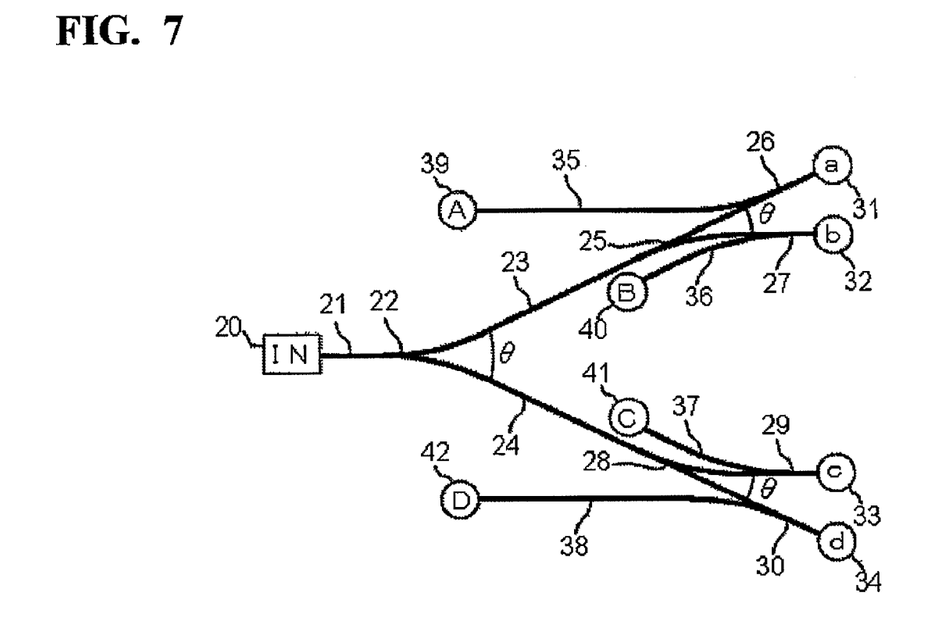
FIG. 7 is a top plan view showing one example of modification of a passage configuration in the gas passage section

FIG. 7 is a top plan view showing one example of modification of the passage configuration in the gas passage section 1. In this modification, two branch (or terminal branch) passages on a downstream side of each of three branch points 22, 25, 28 are arranged at an angle of less than 45 degrees to each other, as with the aforementioned passage configuration, and thereby the sample gas can smoothly flow. Further, in this modification, each passage in a vicinity of each of the branch points 22, 25, 28 is formed in a shape gently curved in a flow direction of the sample gas, and thereby the sample gas can more smoothly flow. This makes it possible to reduce the risk that various components contained in the sample gas attach onto an inner wall surface of the passage, so as to allow the sample gas to reach a desired one of the gas outlets without a change in concentration of each of the components.

Preferably, the inner wall surface of the passage is subjected to an inactivation treatment, such as a silica treatment at a high temperature. This makes it possible to more reliably prevent the attachment of the components of the sample gas onto the inner wall surface of the passage.

An advantageous embodiment of the present invention has been shown and described by way of example. It is obvious to those skilled in the art that various changes and modifications may be made therein without departing from the spirit and scope of the present invention as set forth in appended claims. For example, while the above embodiment has been described based on an example where the number of gas outlets is four, the present invention may be applied to a configuration provided with a gas outlet in any number equal to or greater than three.

What is claimed is:

1. A gas flow path switching unit for setting a gas flow path to allow a target gas introduced from a gas inlet to be discharged from one of a number n of gas outlets, wherein n is an integer equal to or greater than 3, according to control of a supply of a switching gas, said gas flow path switching unit comprising:
   a) a target gas passage for allowing said target gas to pass therethrough, said target gas passage including a main passage having a proximal end serving as said gas inlet, and a number n of branch passages each provided with a respective one of said gas outlets at a terminal end thereof, said branch passages being formed by branching said main passage into two sub passages at a branch point defined by a distal end of said main passage and further branching at least one of said sub passages into two sub-sub passages at a branch point defined by a distal end of said sub passage; and
   b) at least a number n of switching-gas supply passages connected to respective intermediate positions of said n branch passages to supply said switching gas thereto; wherein the number of said at least n switching-gas supply passages connected to respective intermediate positions of said n branch passages is n, wherein said gas flow path switching unit further comprises switching-gas supply control means operable to supply said switching gas to each of said n switching-gas supply passages in such a manner that a gas supply pressure in a specific one of a number n of switching-gas supply ports of said n switching-gas supply passages becomes less than that in the remaining switching-gas supply ports, whereby said target gas is discharged from the gas outlet at the terminal end of one of said branch passages which is supplied with said switching gas from said specific switching-gas supply port at the gas supply pressure less than that in said remaining switching-gas supply ports;

where said switching-gas supply control means includes:

at least a number n−1 of valves each operable to allow said switching gas supplied from a switching-gas entrance thereof to be selectively discharged from one of two switching-gas exits thereof; and at least a number n−1 of resistance tubes each connecting between said two switching-gas exits of a corresponding one of said valves.

2. The gas flow path switching unit as defined in claim 1, wherein said switching-gas supply control means is operable to switch between two flow paths in each of said at least n−1 valves, in such a manner that, in a plurality of switching-gas flows paths set as a result of said switching, said switching gas reaching said specific switching-gas supply port after passing through a largest number of consecutive ones of said resistance tubes has a gas supply pressure less than that in said remaining switching-gas supply ports.

3. The gas flow path switching unit as defined in claim 1, where said switching-gas supply control means further includes:

a switching gas source passage for providing said switching gas to a first valve of the n−1 valves;

two sub switching gas passages that respectively receive said switching gas from the switching-gas exits of the first valve, a first of the n−1 resistance tubes being connected between said two switching-gas exits of said first valve, and one of the sub switching passages providing the switching gas to a second valve of the n−1 valves;

two sub sub switching gas passages that respectively receive said switching gas from the switching-gas exits of the second valve, wherein a second tube of the n−1 resistance tubes is connected between said two switching-gas exits of said second valve.

4. The gas flow path switching unit as defined in claim 1, wherein n is an integer equal to or greater than 4, and the branching as least one of said sub passages comprises branching each of the two sub passages into two sub-sub passages.

5. The gas flow path switching unit as defined in claim 4, wherein wherein said switching-gas supply control means further includes:

a switching gas source passage for providing said switching gas to a first value of the n−1 valves;

two sub switching gas passages that respectively receive said switching gas from the switching-gas exits of the first valve, a first of the n−1 resistance tubes being connected between said two switching-gas exits of said first valve, one of the sub switching passages providing the switching gas to a second valve of the n−1 valves, and another of the sub switching passages providing the switching gas to a third valve of the n−1 valves;

two sub sub switching gas passages that respectively receive said switching gas from the switching-gas exits of the second valve, wherein a second tube of the n−1 resistance tubes is connected between said two switching-gas exits of said second valve; and two sub sub switching gas passages that respectively receive said switching gas from the switching-gas exits of the third valve, wherein a third of the n−1 resistance tubes is connected between said two switching-gas exits of said third valve.

6. The gas flow path switching unit as defined in claim 1, wherein said target gas passage and said switching-gas supply passages include a laminated assembly prepared by sandwiching a first plate-shaped member formed with a cutout portion corresponding to at least a part of said target gas passage and said switching-gas supply passages, between at least two second plate-shaped members.

7. The gas flow path switching unit as defined in claim 6, wherein each of said first and second plate-shaped members is made of metal, and wherein a passage-defining inner surface thereof is subjected to an inactivation treatment.

8. The gas flow path switching unit as defined in claim 6, wherein two of said branch passages branched from the common branch point defined by their proximal ends are arranged at an angle of less than 45 degrees to each other.

9. The gas flow path switching unit as defined in claim 8, wherein each of said first and second plate-shaped members is made of metal, and wherein a passage-defining inner surface thereof is subjected to an inactivation treatment.

* * * * *